(12) United States Patent
Audousset

(10) Patent No.: US 7,871,445 B2
(45) Date of Patent: Jan. 18, 2011

(54) COMPOSITION FOR THE OXIDATION DYEING OF KERATIN FIBERS COMPRISING AT LEAST ONE NONIONIC DERIVATIVE OF CELLULOSE WITH AT LEAST ONE HYDROPHOBIC SUBSTITUENT, AT LEAST ONE OXIDATION BASE OF DIAMINODIAZACYCLOPENTENE TYPE, AND AT LEAST ONE OXIDATION COUPLER, AN OXIDATION DYEING PROCESS, AND KIT

(75) Inventor: Marie-Pascale Audousset, Asnieres (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 12/267,786

(22) Filed: Nov. 10, 2008

(65) Prior Publication Data

US 2009/0151090 A1     Jun. 18, 2009

(30) Foreign Application Priority Data

Nov. 9, 2007    (FR) .................... 07 58914

(51) Int. Cl.
*A61Q 5/10* (2006.01)

(52) U.S. Cl. .................. 8/405; 8/406; 8/409; 8/410; 8/411; 8/421; 8/435; 8/570; 8/573

(58) Field of Classification Search ......... 8/405, 8/406, 410, 409, 411, 421, 435, 570, 573
See application file for complete search history.

(56) References Cited

U.S. PATENT DOCUMENTS

| | | | |
|---|---|---|---|
| 5,061,289 A | 10/1991 | Clausen et al. | |
| 5,380,340 A | 1/1995 | Neunhoeffer et al. | |
| 5,534,267 A | 7/1996 | Neunhoeffer et al. | |
| 6,010,541 A | 1/2000 | De La Mettrie et al. | |
| 7,285,137 B2 | 10/2007 | Vidal et al. | |
| 7,306,630 B2 | 12/2007 | Audousset | |
| 7,329,287 B2 | 2/2008 | Simonet et al. | |
| 7,410,505 B2 | 8/2008 | Cottard et al. | |
| 7,485,156 B2 | 2/2009 | Saunier | |
| 7,569,078 B2 | 8/2009 | Legrand | |
| 2001/0023515 A1* | 9/2001 | Cottard et al. | 8/406 |
| 2001/0047554 A1 | 12/2001 | Mettrie et al. | |
| 2004/0172771 A1 | 9/2004 | Cottard et al. | |
| 2005/0166335 A1* | 8/2005 | Vidal et al. | 8/405 |
| 2005/0169871 A1 | 8/2005 | De La Mettrie | |
| 2006/0260071 A1 | 11/2006 | Legrand | |
| 2007/0050924 A1 | 3/2007 | Cotteret | |

FOREIGN PATENT DOCUMENTS

| | | |
|---|---|---|
| DE | 41 33 957 | 4/1993 |
| DE | 42 34 887 | 4/1994 |
| EP | 0 375 977 | 7/1990 |
| EP | 1 426 038 | 6/2004 |
| EP | 1 426 040 | 6/2004 |
| EP | 1 473 025 | 11/2004 |
| EP | 1 550 656 | 7/2005 |
| EP | 1 566 164 | 8/2005 |
| EP | 1 707 190 | 10/2006 |
| EP | 1 733 716 | 12/2006 |
| WO | WO 98/03150 | 1/1998 |
| WO | WO 02/051372 | 7/2002 |

OTHER PUBLICATIONS

Copending U.S. Appl. No. 12/267,764, filed Nov. 10, 2008.
French Search Report for FR 07/58912, dated Jun. 25, 2008.
French Search Report for FR 07/58914, dated Jun. 17, 2008.
Office Action mailed Jun. 2, 2009, in co-pending U.S. Appl. No. 12/267,764.

* cited by examiner

*Primary Examiner*—Eisa B Elhilo
(74) *Attorney, Agent, or Firm*—Finnegan, Henderson, Farabow, Garrett & Dunner, L.L.P.

(57) ABSTRACT

The present disclosure relates to a dye composition for keratin fibers, such as keratin fibers, for example the hair, comprising, in a medium suitable for dyeing: at least one nonionic derivative of cellulose comprising at least one hydrophobic substituent containing from 8 to 30 carbon atoms; at least one oxidation base chosen from diaminodiazacyclopentene derivatives; and at least one oxidation coupler; and a process for dyeing keratin fibers using such a composition.

22 Claims, No Drawings

COMPOSITION FOR THE OXIDATION DYEING OF KERATIN FIBERS COMPRISING AT LEAST ONE NONIONIC DERIVATIVE OF CELLULOSE WITH AT LEAST ONE HYDROPHOBIC SUBSTITUENT, AT LEAST ONE OXIDATION BASE OF DIAMINODIAZACYCLOPENTENE TYPE, AND AT LEAST ONE OXIDATION COUPLER, AN OXIDATION DYEING PROCESS, AND KIT

This application claims benefit of priority under 35 U.S.C. §119 to French Patent Application No. FR 0758914, filed Nov. 9, 2007, the contents of which are incorporated herein by reference.

The present disclosure relates to a composition for the oxidation dyeing of keratin fibers, such as human keratin fibers for example, the hair comprising at least one nonionic derivative of cellulose modified with at least one hydrophobic group, at least one dye of diaminodiazacyclopentene type, and at least one oxidation coupler.

The disclosure also relates to the use of this composition for dyeing keratin fibers and also to the dyeing process using this composition.

It is known practice to dye keratin fibers, such as human hair, with dye compositions comprising oxidation dye precursors, generally known as oxidation bases, such as ortho- or para-phenylenediamines, ortho- or para-aminophenols, and heterocyclic compounds. These oxidation bases are colorless or weakly colored compounds which, in combination with oxidizing products, can give rise, via an oxidative condensation process, to colored compounds.

It is also known practice to vary the shades obtained with these oxidation bases by combining them with couplers or coloring modifiers, the latter being chosen from, for example, aromatic meta-diamines, meta-aminophenols, meta-diphenols, and certain heterocyclic compounds, such as indole compounds.

The variety of the molecules available as oxidation bases and couplers can make it possible to obtain a rich palette of colors.

It is desirable that the "permanent" coloring obtained by virtue of these oxidation dyes should, moreover, meet a certain number of requirements.

For instance, it should have no toxicological drawbacks; it should allow shades to be obtained in the desired strength; and it should show good color-fastness with respect to external agents such as light, bad weather, washing, permanent-waving, perspiration, and rubbing.

In addition, the dyes should also allow white hair to be covered and, finally, should be as nonselective as possible, i.e., they should make it possible to obtain the smallest possible differences in coloring along the same keratin fiber, which is generally differently sensitized (i.e., damaged) between its tip and its root.

Moreover, the compositions obtained should, in addition, have good rheological properties, while at the same time conserve good coloring properties. For instance, these compositions should not run on the face or out of the areas intended to be dyed, when they are applied, such as after mixing with an oxidizing agent.

Improving the power of dyeing by combining a para-phenylenediamine oxidation base and at least one nonionic amphiphilic polymer such as hydroxycellulose modified with a hydrophobic group is discussed in International Patent Application Publication No. WO 98/03150.

However, these compositions do not entirely meet the abovementioned requirements and can be improved, for example, in terms of dyeing properties, such as selectivity and fastness.

Thus, there is a need in the art to obtain stable hair dyeing compositions, such as in the form of creams, which are easy to prepare and apply, which have good rheological properties and which produce colorations that are strong and relatively nonselective and that withstand the various attacks to which keratin fibers may be subjected.

Accordingly, one aspect of the present disclosure is a dye composition for keratin fibers, such as human keratin fibers, for instance the hair, that meets at least one of the conditions discussed above, comprising, in a medium suitable for dyeing:

(A) at least one nonionic derivative of cellulose comprising at least one hydrophobic substituent containing from 8 to 30 carbon atoms;

(B) at least one oxidation base chosen from diaminodiazacyclopentene derivatives, and addition salts thereof; and (C) at least one oxidation coupler.

The dye compositions according to the present disclosure may have at least one of the following properties:

they make it possible to obtain compositions with a viscosity of a cream, which are stable over time, they stand out by virtue of the fact that they could be easily mixed with the oxidizing composition, they stand out by virtue of the rheological qualities of the creams obtained (good viscosity of cream as a mixture), and they are easy to apply after mixing with the oxidizing composition at the time the dyeing is carried out (qualities of use on the head).

In addition, the compositions according to the present disclosure can make it possible to obtain compositions capable of producing colorings with varied, chromatic, powerful, aesthetic, and relatively nonselective shades which are uniform over all the keratin fibers, for example human keratin fibers, such as the hair, and which are highly resistant to the various attacks to which the fibers may be subjected.

Another aspect of the present disclosure comprises a process for dyeing keratin fibers, wherein the cosmetic composition according to the present disclosure is used.

Yet another aspect of the present disclosure relates to the use of this cosmetic composition for dyeing keratin fibers, for instance human keratin fibers, such as the hair.

Other features, aspects, subjects, and benefits of the present disclosure will emerge more clearly on reading the description and the non-limiting examples which follow.

Unless otherwise indicated, the limits of the ranges of values which are given in the context of the present disclosure are included in these ranges.

As used herein, the term "derivative of cellulose" is intended to mean at least one compound comprising at least one cellobiose unit having the following structure:

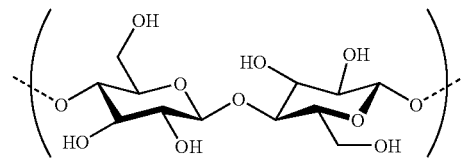

wherein at least one hydroxyl group may be substituted.

The at least one nonionic derivative of cellulose comprising at least one hydrophobic substituent (A) in accordance with the present disclosure is an amphiphilic polymer that is associative in nature. It comprises hydrophilic units and hydrophobic units and is capable of interacting and of associating with one another or with other molecules, reversibly, such as, by virtue of the presence of their hydrophobic chains.

According to at least one embodiment of the present disclosure, the at least one cellulose derivative of the present disclosure is a cellulose ether comprising at least one hydrophobic substituent comprising from 8 to 30 carbon atoms.

The at least one nonionic derivative of cellulose with at least one hydrophobic substituent in accordance with the present disclosure, can be prepared from water-soluble nonionic ethers of cellulose, wherein all or some of the reactive hydroxyl functional groups are substituted with at least one hydrophobic chain comprising from 8 to 30 carbon atoms, for example, comprising from 10 to 22 carbon atoms, and further for example, comprising 16 carbon atoms. The reaction steps involved in the preparation of the at least one cellulose derivative of the present disclosure are known to those skilled in the art.

The nonionic ethers of cellulose chosen for preparing the at least one nonionic derivative of cellulose with at least one hydrophobic substituent, according to the present disclosure, can have a degree of nonionic substitution, for example a methyl, hydroxyethyl, or hydroxypropyl group, that is sufficiently water-soluble, i.e., forms a substantially clear solution when dissolved in water at 25° C. in an amount of 1% by weight.

The nonionic ethers of cellulose chosen for preparing the at least one nonionic derivative of cellulose with at least one hydrophobic substituent, according to the present disclosure, can have, for example, a relatively low number-average molar mass, such as less than 800,000 g/mol, for instance, ranging from 50,000 to 700,000 g/mol, and further for example, ranging from 200,000 to 600,000 g/mol.

According to at least one embodiment of the present disclosure, the at least one nonionic cellulose derivative of the present disclosure is a hydroxyethylcellulose comprising at least one hydrophobic substituent containing from 8 to 30 carbon atoms.

The at least one nonionic derivative of cellulose according to the present disclosure is substituted with at least one entity chosen from aliphatic and aromatic, saturated and unsaturated, linear, branched, and cyclic $C_8$-$C_{30}$ hydrocarbon chain, that may be attached to the cellulose ether substrate via an ether, ester, or urethane bond, and in at least one embodiment of the present disclosure, via an ether bond.

According to at least one embodiment, the hydrophobic substituents used as the at least one hydrophobic substituent of the at least one nonionic derivative of cellulose according to the present disclosure are chosen from $C_8$-$C_{30}$, for example, $C_{10}$-$C_{22}$, alkyl, arylalkyl, and alkylaryl groups.

In another embodiment, the at least one hydrophobic substituent according to the present disclosure can be chosen from saturated alkyl chains.

According to at least one embodiment, the at least one hydrophobic substituent according to the present disclosure can be chosen from cetyl groups.

The at least one nonionic derivative of cellulose with at least one hydrophobic substituent according to the present disclosure has a viscosity ranging from 100 to 100,000 mPa·s, such as ranging from 200 to 20,000 mPa·s, measured at 25° C. in a solution at 1% by weight of polymer in water, this viscosity being determined conventionally using a Brookfield LVT viscometer at 6 rpm with the No. 3 spindle.

The degree of hydrophobic substitution of the hydrophilic nonionic derivatives of cellulose used according to the present disclosure can range, for example, from 0.1% to 10% by weight, for example from 0.1% to 1% by weight, and further for example from 0.4% to 0.8% by weight, relative to the total weight of the polymer.

Non-limiting examples of the at least one nonionic derivative of cellulose with at least one hydrophobic substituent of the present disclosure include cetyl hydroxyethylcelluloses sold, for instance, under the names NATROSOL® PLUS GRADE 330 CS and POLYSURF® 67 CS (INCI: Cetyl Hydroxyethylcellulose) by the company Aqualon/Hercules.

The at least one nonionic derivative of cellulose with at least one hydrophobic substituent (A) according to the present disclosure can be present in an amount ranging from 0.01% to 10% by weight, such as from 0.05% to 3% by weight, and further for example from 0.1% to 1% by weight, relative to the total weight of the composition.

As used herein, the term "diaminodiazacyclopentene derivative" is intended to mean at least one compound comprising in its molecular structure the following substructure:

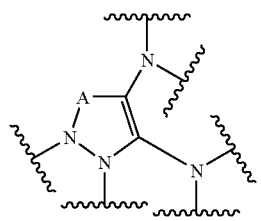

wherein A is chosen from carbonyl groups, carbon atoms bearing a hydrogen atom, and another substituent.

In at least one embodiment, the diaminodiazacyclopentene derivative is a diaminopyrazolone derivative or a diaminopyrazole derivative.

According to the present disclosure, the term "diaminopyrazolone derivative" is intended to mean at least one compound comprising in its molecular structure the following substructure:

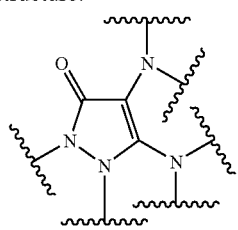

The diaminopyrazolone derivatives are derivatives of 4,5-diaminopyrazol-3-one or 2,3-diaminopyrazol-1-one.

The diaminopyrazolone derivatives according to the present disclosure are chosen from, in at least one embodiment, compounds of formula (I) below:

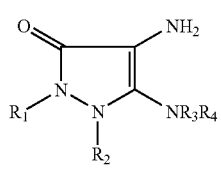

(I)

wherein:
$R_1$, $R_2$, $R_3$, and $R_4$, which may be identical or different, are independently chosen from;
hydrogen atoms;
linear and branched $C_1$-$C_{10}$ alkyl groups, such as $C_1$-$C_6$ alkyl groups, wherein the alkyl group is optionally substituted with at least one group chosen from OR$_5$, NR$_6$R$_7$, carboxyl groups, sulfonic, carboxamido CONR$_6$R$_7$, sulfonamido SO$_2$NR$_6$R$_7$ groups, aliphatic heterocycles such as piperidine, and aryls optionally substituted with at least one group chosen from C$_1$-C$_4$ alkyl, hydroxyl, C$_1$-C$_2$ alkoxy, amino, and (di)(C$_1$-C$_2$) alkylamino groups;

aryl groups optionally substituted with at least one group chosen from C$_1$-C$_4$ alkyl, hydroxyl, C$_1$-C$_2$ alkoxy, amino, and (di)(C$_1$-C$_2$)alkylamino groups; and heteroaryl groups comprising 5 or 6 ring members, optionally substituted with at least one group chosen from C$_1$-C$_4$ alkyl and C$_1$-C$_2$ alkoxy groups;

R$_5$, R$_6$, and R$_7$, which may be identical or different, are independently chosen from:

hydrogen atoms;

linear and branched C$_1$-C$_4$, for example C$_1$-C$_2$, alkyl groups, optionally substituted with at least one group chosen from hydroxyl, C$_1$-C$_2$ alkoxy, carboxamido CONR$_8$R$_9$, sulfonyl SO$_2$R$_8$, and aryl groups optionally substituted with a group chosen from C$_1$-C$_4$ alkyl, hydroxyl, C$_1$-C$_2$ alkoxy, amino, and (di)(C$_1$-C$_2$)alkylamino groups;

aryl groups optionally substituted with at least one group chosen from C$_1$-C$_4$ alkyl, hydroxyl, C$_1$-C$_2$ alkoxy, amino, and (di)(C$_1$-C$_2$)alkylamino groups;

carboxamido groups CONR$_8$R$_9$; and sulfonyl groups SO$_2$R$_8$;

R$_8$ and R$_9$, which may be identical or different, are independently chosen from hydrogen atoms; and linear and branched C$_1$-C$_4$ alkyl groups optionally substituted with at least one group chosen from hydroxyl and C$_1$-C$_2$ alkoxy groups;

R$_1$ and R$_2$, on the one hand, and R$_3$ and R$_4$, on the other hand, may also form, together with the nitrogen atom(s) to which they are attached, a saturated or unsaturated heterocycle comprising from 5 to 7 ring members, optionally substituted or N-substituted with at least one group chosen from halogen atoms, amino, (di)(C$_1$-C$_4$) alkylamino, (di)hydroxy(C$_1$-C$_2$)alkylamino, hydroxyl, carboxyl, carboxamido, (di)(C$_1$-C$_2$)alkylcarboxamido and C$_1$-C$_2$ alkoxy groups, and C$_1$-C$_4$ alkyl groups optionally substituted with at least one group chosen from hydroxyl, amino, (di)alkylamino, alkoxy, carboxyl, and sulfonyl groups; it being possible for said heterocycles formed by R$_1$ and R$_2$, on the one hand, and R$_3$ and R$_4$, on the other hand, with the nitrogen atom(s) to which they are attached, to be identical or different, and it being possible for the ring members forming said heterocycles to be chosen, for example, from carbon, nitrogen, and oxygen atoms.

According to at least one embodiment of the present disclosure, R$_1$ and R$_2$, which may be identical or different, are independently chosen from:

C$_1$-C$_6$ alkyl groups optionally substituted with at least one group chosen from hydroxyl, C$_1$-C$_2$ alkoxy, amino, and (di)(C$_1$-C$_2$)alkylamino groups; and phenyl, methoxyphenyl, ethoxyphenyl, and benzyl groups.

In one embodiment of the present disclosure, R$_1$ and R$_2$, which may be identical or different, are independently chosen from methyl, ethyl, 2-hydroxyethyl, 3-hydroxypropyl, 2-hydroxypropyl, and phenyl groups.

According to another embodiment of the present disclosure, R$_1$ and R$_2$ form, together with the nitrogen atoms to which they are attached, a saturated or unsaturated, 5- or 6-membered ring optionally substituted with at least one group chosen from halogen atoms, amino, (di)(C$_1$-C$_4$)alkylamino, (di)hydroxy(C$_1$-C$_2$)alkylamino, hydroxyl, carboxyl, carboxamido, (di)(C$_1$-C$_2$) alkylcarboxamido and C$_1$-C$_2$ alkoxy groups, and C$_1$-C$_4$ alkyl groups optionally substituted with at least one group chosen from hydroxyl, amino, (di) alkylamino, alkoxy, carboxyl, and sulfonyl groups.

In yet another embodiment of the present disclosure, R$_1$ and R$_2$ form, together with the nitrogen atoms to which they are attached, a pyrazolidine or pyridazolidine ring optionally substituted with at least one group chosen from C$_1$-C$_4$ alkyl, hydroxyl, C$_1$-C$_2$ alkoxy, carboxyl, carboxamido, amino, and (di)(C$_1$-C$_2$)alkylamino groups.

In another embodiment of the present disclosure, R$_1$ and R$_2$ form, together with the nitrogen atoms to which they are attached, a pyrazolidine or pyridazolidine ring optionally substituted with at least one group chosen from C$_1$-C$_4$ alkyl, hydroxyl, C$_1$-C$_2$ alkoxy, carboxyl, carboxamido, amino, and (di)(C$_1$-C$_2$)alkylamino groups.

According to still another embodiment of the present disclosure, R$_1$ and R$_2$ form, together with the nitrogen atoms to which they are attached, a pyrazolidine, pyridazoline, or pyridazolidine ring.

According to at least one embodiment of the present disclosure, R$_3$ and R$_4$, which may be identical or different, are independently chosen, for example, from a hydrogen atom; linear and branched C$_1$-C$_6$ alkyl groups, optionally substituted with at least one group chosen from hydroxyl, C$_1$-C$_2$ alkoxy, amino and (di)(C$_1$-C$_2$)alkylamino groups and aliphatic heterocycles such as piperidine; and phenyl groups optionally substituted with at least one group chosen from hydroxyl, amino, and C$_1$-C$_2$ alkoxy groups.

In another embodiment of the present disclosure, R$_3$ and R$_4$, which may be identical or different, are independently chosen from a hydrogen atom, and methyl, ethyl, isopropyl, 2-hydroxyethyl, 3-hydroxypropyl, 2-hydroxypropyl, 2-carboxyethyl, 2-dimethylaminoethyl, pyrrolidin-1-yl, 3-hydroxypyrrolidin-1-yl, 4-piperidin-1-yl, 4-methylpiperidin-1-yl, and 3-dimethylaminopiperidin-1-yl groups.

According to another embodiment of the present disclosure, R$_3$ and R$_4$ are hydrogen atoms.

In at least one embodiment of the present disclosure, R$_3$ and R$_4$ form, together with the nitrogen atom to which they are attached, a ring comprising from 5 to 7 members chosen from heterocycles, for instance pyrrolidine, piperidine, homopiperidine, piperazine, and homopiperazine; it being possible for said ring to be substituted or N-substituted with at least one group chosen from hydroxyl, amino, (di)(C$_1$-C$_2$) alkylamino, (di)hydroxy(C$_1$-C$_2$)alkylamino, carboxyl, carboxamido, (di)(C$_1$-C$_2$)alkylcarboxamido, and C$_1$-C$_4$ alkyl groups, optionally substituted with at least one group chosen from hydroxyl, amino, and C$_1$-C$_2$ (di)alkylamino groups.

In yet another embodiment of the present disclosure, R$_3$ and R$_4$ form, together with the nitrogen atom to which they are attached, a ring comprising from 5 to 7 members, chosen from pyrrolidine, 2,5-dimethylpyrrolidine, pyrrolidine-2-carboxylic acid, 3-hydroxypyrrolidine-2-carboxylic acid, 4-hydroxypyrrolidine-2-carboxylic acid, 2,4-dicarboxypyrrolidine, 3-hydroxy-2-hydroxymethylpyrrolidine, 2-carboxamidopyrrolidine, 3-hydroxy-2-carboxamidopyrrolidine, 2-(diethylcarboxamido)pyrrolidine, 2-hydroxymethylpyrrolidine, 3,4-dihydroxy-2-hydroxymethylpyrrolidine, 3-hydroxypyrrolidine, 3,4-dihydroxypyrrolidine, 3-aminopyrrolidine, 3-methylaminopyrrolidine, 3-dimethylaminopyrrolidine, 4-amino-3-hydroxypyrrolidine, 3-hydroxy-4-(2-hydroxyethyl)aminopyrrolidine, piperidine, 2,6-dimethylpiperidine, 2-carboxypiperidine, 2-carboxamidopiperidine, 2-hydroxymethylpiperidine, 3-hydroxy-2-hydroxymethylpiperidine, 2-hydroxypiperidine, 3-hydroxypiperidine, 4-hydroxypiperidine, 3-hydroxymethylpiperidine, homopiperidine, 2-carboxyhomopiperidine, 2-carboxamidohomopiperidine, homopiperazine, N-methylhomopiperazine, and N-(2-hydroxyethyl)homopiperazine.

For example, $R_3$ and $R_4$ form, together with the nitrogen atom to which they are attached, a ring comprising from 5 to 7 members, chosen from pyrrolidine, 3-hydroxypyrrolidine, 3-aminopyrrolidine, 3-dimethylaminopyrrolidine, pyrrolidine-2-carboxylic acid, 3-hydroxypyrrolidine-2-carboxylic acid, piperidine, hydroxypiperidine, homopiperidine, 1,4-diazepane, N-methylhomopiperazine, and N-β-hydroxyethylhomopiperazine.

In accordance with at least one embodiment of the present disclosure, $R_3$ and $R_4$ form, together with the nitrogen atom to which they are attached, a 5-membered ring such as pyrrolidine, 3-hydroxypyrrolidine, 3-aminopyrrolidine, or 3-dimethylaminopyrrolidine.

The compounds of formula (I) may be optionally salified with strong mineral acids, such as HCl, HBr, HI, $H_2SO_4$, or $H_3PO_4$, or organic acids such as acetic acid, lactic acid tartaric acid, citric acid, succinic acid, benzenesulfonic acid, paratoluenesulfonic acid, formic acid, or methanesulfonic acid.

They may also be in the form of solvates, for example a hydrate, or a solvate of a linear or branched alcohol, such as ethanol or isopropanol.

Non-limiting examples of derivatives of formula (I) that may be mentioned include:
4,5-diamino-1,2-dimethyl-1,2-dihydropyrazol-3-one;
4-amino-5-methylamino-1,2-dimethyl-1,2-dihydropyrazol-3-one;
4-amino-5-dimethylamino-1,2-dimethyl-1,2-dihydropyrazol-3-one;
4-amino-5-(2-hydroxyethyl)amino-1,2-dimethyl-1,2-dihydropyrazol-3-one;
4-amino-5-(pyrrolidin-1-yl)-1,2-dimethyl-1,2-dihydropyrazol-3-one;
4-amino-5-(piperidin-1-yl)-1,2-dimethyl-1,2-dihydropyrazol-3-one;
4,5-diamino-1,2-di-(2-hydroxyethyl)-1,2-dihydropyrazol-3-one;
4-amino-5-methylamino-1,2-di-(2-hydroxyethyl)-1,2-dihydropyrazol-3-one;
4-amino-5-dimethylamino-1,2-di-(2-hydroxyethyl)-1,2-dihydropyrazol-3-one;
4-amino-5-(2-hydroxyethyl)amino-1,2-di-(2-hydroxyethyl)-1,2-dihydropyrazol-3-one;
4-amino-5-(pyrrolidin-1-yl)-1,2-di-(2-hydroxyethyl)-1,2-dihydropyrazol-3-one;
4-amino-5-(piperidin-1-yl)-1,2-di-(2-hydroxyethyl)-1,2-dihydropyrazol-3-one;
4,5-diamino-1,2-diethyl-1,2-dihydropyrazol-3-one;
4,5-diamino-1,2-diphenyl-1,2-dihydropyrazol-3-one;
4,5-diamino-1-ethyl-2-methyl-1,2-dihydropyrazol-3-one;
4,5-diamino-2-ethyl-1-methyl-1,2-dihydropyrazol-3-one;
4,5-diamino-1-phenyl-2-methyl-1,2-dihydropyrazol-3-one;
4,5-diamino-2-phenyl-1-methyl-1,2-dihydropyrazol-3-one;
4,5-diamino-1-(2-hydroxyethyl)-2-methyl-1,2-dihydropyrazol-3-one;
4,5-diamino-2-(2-hydroxyethyl)-1-methyl-1,2-dihydropyrazol-3-one;
2,3-diamino-6,7-dihydro-1H,5H-pyrazolo[1,2-a]pyrazol-1-one;
2-amino-3-methylamino-6,7-dihydro-1H,5H-pyrazolo[1,2-a]pyrazol-1-one;
2-amino-3-dimethylamino-6,7-dihydro-1H,5H-pyrazolo[1,2-a]pyrazol-1-one;
2-amino-3-ethylamino-6,7-dihydro-1H,5H-pyrazolo[1,2-a]pyrazol-1-one;
2-amino-3-isopropylamino-6,7-dihydro-1H,5H-pyrazolo[1,2-a]pyrazol-1-one;
2-amino-3-(2-hydroxyethyl)amino-6,7-dihydro-1H,5H-pyrazolo[1,2-a]pyrazol-1-one;
2-amino-3-(2-hydroxypropyl)amino-6,7-dihydro-1H,5H-pyrazolo[1,2-a]pyrazol-1-one;
2-amino-3-bis(2-hydroxyethyl)amino-6,7-dihydro-1H,5H-pyrazolo[1,2-a]pyrazol-1-one;
2-amino-3-(pyrrolidin-1-yl)-6,7-dihydro-1H,5H-pyrazolo[1,2-a]pyrazol-1-one;
2-amino-3-(3-hydroxy-pyrrolidin-1-yl)-6,7-dihydro-1H,5H-pyrazolo[1,2-a]pyrazol-1-one;
2-amino-3-(piperidin-1-yl)-6,7-dihydro-1H,5H-pyrazolo[1,2-a]pyrazol-1-one;
2,3-diamino-6-hydroxy-6,7-dihydro-1H,5H-pyrazolo[1,2-a]pyrazol-1-one;
2,3-diamino-6-methyl-6,7-dihydro-1H,5H-pyrazolo[1,2-a]pyrazol-1-one;
2,3-diamino-6,6-dimethyl-6,7-dihydro-1H,5H-pyrazolo[1,2-a]pyrazol-1-one;
2,3-diamino-5,6,7,8-tetrahydro-1H,6H-pyridazino[1,2-a]pyrazol-1-one;
2,3-diamino-5,8-dihydro-1H,6H-pyridazino[1,2-a]pyrazol-1-one;
4-amino-5-dimethylamino-1,2-diethyl-1,2-dihydropyrazol-3-one;
4-amino-1,2-diethyl-5-ethylamino-1,2-dihydropyrazol-3-one;
4-amino-1,2-diethyl-5-isopropylamino-1,2-dihydropyrazol-3-one;
4-amino-1,2-diethyl-5-(2-hydroxyethylamino)-1,2-dihydropyrazol-3-one;
4-amino-5-(2-dimethylaminoethylamino)-1,2-diethyl-1,2-dihydropyrazol-3-one;
4-amino-5-[bis(2-hydroxyethyl)amino]-1,2-diethyl-1,2-dihydropyrazol-3-one;
4-amino-1,2-diethyl-5-(3-imidazol-1-yl-propylamino)-1,2-dihydropyrazol-3-one;
4-amino-1,2-diethyl-5-(3-hydroxypyrrolidin-1-yl)-1,2-dihydropyrazol-3-one;
4-amino-5-pyrrolidin-1-yl-1,2-diethyl-1,2-dihydropyrazol-3-one;
4-amino-5-(3-dimethylaminopyrrolidin-1-yl)-1,2-diethyl-1,2-dihydropyrazol-3-one; and
4-amino-1,2-diethyl-5-(4-methylpiperazin-1-yl)pyrazolidin-3-one; and their addition salts thereof;

some of which appear below so as to illustrate, in a non-limiting manner, the names with chemical structures:

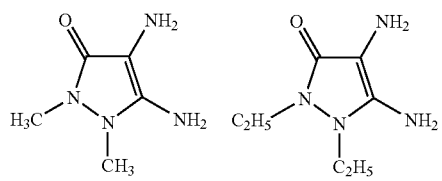

4,5-diamino-1,2-dimethyl-1,2-dihydro-pyrazol-3-one 4,5-diamino-1,2-diethyl-1,2-dihydro-pyrazol-3-one

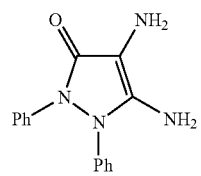
4,5-diamino-1,2-diphenyl-
1,2-dihydro-pyrazol-3-one

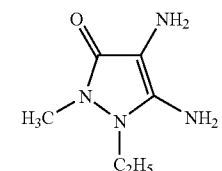
4,5-diamino-1-ethyl-2-methyl-
1,2-dihydropyrazol-3-one

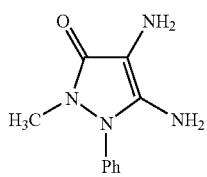
4,5-diamino-1-phenyl-2-methyl-
1,2-dihydropyrazol-3-one

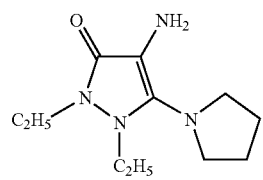
4-amino-5-(pyrrolidin-1-yl)-1,2-diethyl-
1,2-dihydropyrazol-3-one

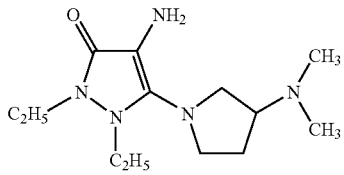
4-amino-5-(3-dimethylaminopyrrolidin-1-yl)-1,2-
diethyl-1,2-dihydropyrazol-3-one

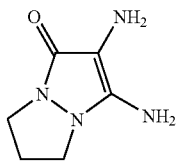
2,3-diamino-6,7-dihydro-1H,5H-pyrazolo
[1,2-a]pyrazol-1-one

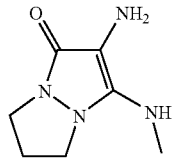
2-amino-3-methylamino-6,7-dihydro-
1H,5H-pyrazolo[1,2-a]pyrazol-1-one

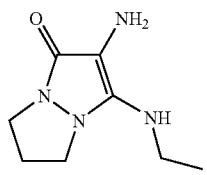
2-amino-3-ethylamino-6,7-dihydro-
1H,5H-pyrazolo[1,2-a]pyrazol-1-one

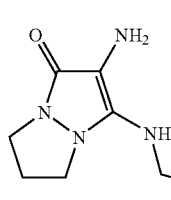
2-amino-3-(2-hydroxyethyl)amino-6,7-dihydro-
1H,5H-pyrazolo[1,2-a]pyrazol-1-one

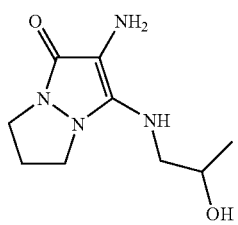
2-amino-3-(2-hydroxypropyl)amino-6,7-
dihydro-1H,5H-pyrazolo[1,2-a]pyrazol-1-one

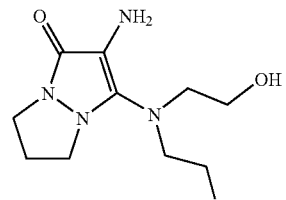
2-amino-3-bis(2-hydroxyethyl)amino-6,7-dihydro-
1H,5H-pyrazolo[1,2-a]pyrazol-1-one

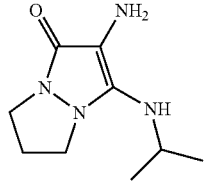
2-amino-3-isopropylamino-6,7-dihydro-
1H,5H-pyrazolo[1,2-a]pyrazol-1-one

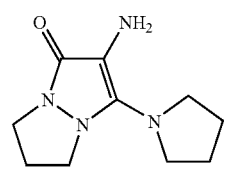
2-amino-3-(pyrrolidin-1-yl)-6,7-dihydro-
1H,5H-pyrazolo[1,2-a]pyrazol-1-one

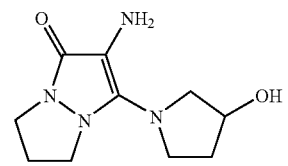
2-amino-3-(3-hydroxypyrrolidin-1-yl)-6,7-dihydro-
1H,5H-pyrazolo[1,2-a]pyrazol-1-one -continued

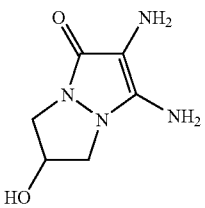

2,3-diamino-6-hydroxy-6,7-dihydro-
1H,5H-pyrazolo[1,2-a]pyrazol-1-one

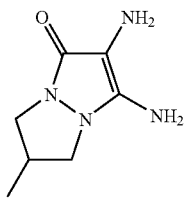

2,3-diamino-6-methyl-6,7-dihydro-
1H,5H-pyrazolo[1,2-a]pyrazol-1-one

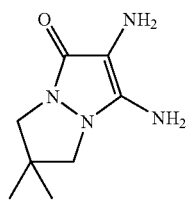

2,3-diamino-6,6-dimethyl-6,7-dihydro-
1H,5H-pyrazolo[1,2-a]pyrazol-1-one

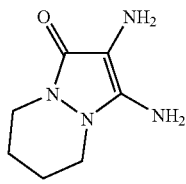

2,3-diamino-5,6,7,8-tetrahydro-
1H,6H-pyridazino[1,2-a]pyrazol-1-one

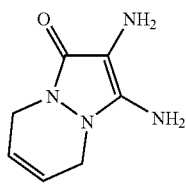

2,3-diamino-5,8-dihydro-
1H,6H-pyridazino[1,2-a]pyrazol-1-one

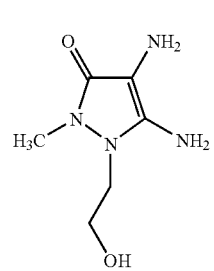

4,5-diamino-1-(2-hydroxyethyl)-2-methyl-
1,2-dihydropyrazol-3-one

-continued

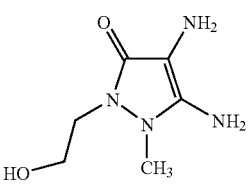

4,5-diamino-2-(2-hydroxyethyl)-1-methyl-
1,2-dihydropyrazol-3-one

Among these compounds, the diaminopyrazolone derivatives of formula (I) include, but are not limited to:

2,3-diamino-6,7-dihydro-1H,5H-pyrazolo[1,2-a]pyrazol-1-one;

2-amino-3-ethylamino-6,7-dihydro-1H,5H-pyrazolo[1,2-a]pyrazol-1-one;

2-amino-3-isopropylamino-6,7-dihydro-1H,5H-pyrazolo[1,2-a]pyrazol-1-one;

2-amino-3-(pyrrolidin-1-yl)-6,7-dihydro-1H,5H-pyrazolo[1,2-a]pyrazol-1-one;

4,5-diamino-1,2-dimethyl-1,2-dihydropyrazol-3-one;

4,5-diamino-1,2-diethyl-1,2-dihydropyrazol-3-one;

4,5-diamino-1,2-di-(2-hydroxyethyl)-1,2-dihydropyrazol-3-one;

2-amino-3-(2-hydroxyethyl)amino-6,7-dihydro-1H,5H-pyrazolo[1,2-a]pyrazol-1-one;

2-amino-3-dimethylamino-6,7-dihydro-1H,5H-pyrazolo[1,2-a]pyrazol-1-one;

2,3-diamino-5,6,7,8-tetrahydro-1H,6H-pyridazino[1,2-a]pyrazol-1-one 4-amino-1,2-diethyl-5-pyrrolidin-1-yl-1,2-dihydropyrazol-3-one;

4-amino-5-(3-dimethylamino-pyrrolidin-1-yl)-1,2-diethyl-1,2-dihydropyrazol-3-one; and 2,3-diamino-6-hydroxy-6,7-dihydro-1H,5H-pyrazolo[1,2-a]pyrazol-1-one.

In at least one embodiment of the present disclosure, the diaminopyrazolone derivatives of formula (I) are chosen from 2,3-diamino-6,7-dihydro-1H,5H-pyrazolo[1,2-a]pyrazol-1-one and salts thereof, such as 2,3-diamino-6,7-dihydro-1H,5H-pyrazolo[1,2-a]pyrazol-1-one dimethane sulfonate of formula:

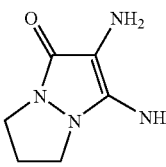

·2(CH₃SO₃H)

As used herein, the term "diaminopyrazole derivative" is intended to mean at least one compound comprising in its molecular structure the following substructure:

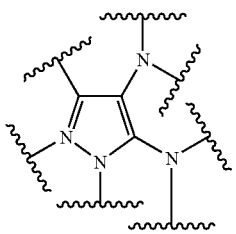

The diaminopyrazole derivative is therefore a derivative of 4,5-diaminopyrazole.

The diaminopyrazole derivative according to at least one embodiment of the present disclosure, is chosen from compounds of formula (II):

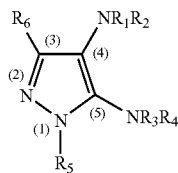

wherein:

$R_1$, $R_2$, $R_3$, $R_4$, and $R_5$, which may be identical or different, are independently chosen from hydrogen atoms; $C_1$-$C_6$ alkyl radicals optionally substituted with at least one substituent chosen from OR, NHR, NRR', SR, SOR, $SO_2R$, COR, COOH, $CONH_2$, CONHR, CONRR', $PO(OH)_2$, SH, $SO_3X$, a noncationic heterocycle, Cl, Br, and I;

X is chosen from a hydrogen atom, Na, K, and $NH_4$; and

R and R', which may be identical or different, are independently chosen from $C_1$-$C_4$ alkyl and alkenyl groups; $C_2$-$C_4$ hydroxyalkyl radicals; $C_2$-$C_4$ aminoalkyl radicals; phenyl radicals optionally substituted with a group chosen from halogen atoms, $C_1$-$C_4$ alkyl, $C_1$-$C_4$ alkoxy, nitro, trifluoromethyl, amino, and $C_1$-$C_4$ alkylamino radicals; benzyl radical optionally substituted with a group chosen from halogen atoms, $C_1$-$C_4$ alkyl, $C_1$-$C_4$ alkoxy, methylenedioxy, and amino radicals; and radicals:

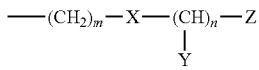

wherein m and n are integers, which may be identical or different, ranging from 0 and 3 inclusive, X is chosen from an oxygen atom and a group NH, Y is chosen from a hydrogen atom and $C_1$-$C_4$ alkyl radicals, and Z is a methyl radical wherein n is equal to 0, or Z is chosen from $C_1$-$C_4$ alkyl radicals, OR, and NR"R''', and when n is greater than or equal to 1, R" and R''', which may be identical or different, are chosen from hydrogen atoms and $C_1$-$C_4$ alkyl radicals; or $R_9$ forms, with the nitrogen atom of the $NR_7R_8$ group at position 5, a heterocycle comprising at least 4 ring members, $R_6$ is chosen from $C_1$-$C_6$ alkyl radicals, $C_1$-$C_4$ hydroxyalkyl radicals; $C_1$-$C_4$ aminoalkyl radicals; ($C_1$-$C_4$)alkylamino($C_1$-$C_4$)alkyl radicals; di($C_1$-$C_4$)alkylamino($C_1$-$C_4$)alkyl radicals; hydroxy($C_1$-$C_4$)alkylamino ($C_1$-$C_4$) alkyl radicals; ($C_1$-$C_4$)alkoxymethyl radicals; phenyl radicals optionally substituted with a group chosen from halogen atoms, ($C_1$-$C_4$)alkyl, ($C_1$-$C_4$)alkoxy, nitro, trifluoromethyl, amino, and ($C_1$-$C_4$)alkylamino radicals; benzyl radicals optionally substituted with a group chosen from halogen atoms, ($C_1$-$C_4$)alkyl, ($C_1$-$C_4$)alkoxy, nitro, trifluoromethyl, amino, and ($C_1$-$C_4$)alkylamino radicals; heterocycles chosen from thiophene, furan, and pyridine, and —$(CH_2)_p$—O—$(CH_2)_q$—OR" radicals, wherein p and q are integers, which may be identical or different, ranging from 1 and 3 inclusive, and R" is as defined above, it being understood that at least one of the radicals $R_1$, $R_2$, $R_3$, and $R_4$ is a hydrogen atom.

The compounds of formula (II) may be optionally salified with strong mineral acids, such as HCl, HBr, $H_1$, $H_2SO_4$, or $H_3PO_4$, or organic acids, such as acetic acid, lactic acid, tartaric acid, citric acid, succinic acid, benzenesulfonic acid, para-toluenesulfonic acid, formic acid, or methanesulfonic acid.

They may also be in the form of solvates, for example, a hydrate, or a solvate of a linear or branched alcohol, such as ethanol or isopropanol.

Derivatives of formula (II) that can be used according to the present disclosure, include, but are not limited to, the compounds described in German Patent Nos. DE-A-38 43 892, DE-A-41 33 957, and DE-A-195 43 988, International Patent Application Nos. WO 94/08969 and WO 94/08970, and French Application No. FR-A-2 733 749, for instance, 4,5-diamino-1-methylpyrazole, 4,5-diamino-1-(2-hydroxyethyl)pyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, and addition salts thereof.

Other useful non-limiting examples of derivatives of formula (II) include 4,5-diamino-1-(2-hydroxyethyl)-1H-pyrazole and salts thereof, such as 4,5-diamino-1-(2-hydroxyethyl)-1H-pyrazole sulfate of formula:

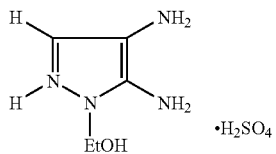

According to the present disclosure, the oxidation bases of diaminodiazacyclopentene type may be present alone or as a mixture in the compositions of the present disclosure.

The at least one oxidation base (B) of diaminodiazacyclopentene type can be present in a total amount ranging from 0.001% to 20% by weight, for example from 0.005% to 10% by weight, and further for example from 0.01% to 5% by weight, relative to the total weight of the composition.

The at least one oxidation coupler (C) according to the present disclosure may be chosen from benzene couplers, heterocyclic couplers, naphthalene couplers, and addition salts thereof.

Benzene couplers that can be used in the compositions according to the present disclosure, include, by way of non-limiting example, meta-aminophenols, meta-phenylenediamines, meta-diphenols, and addition salts thereof.

Among these oxidative couplers, mention may be made, in a non-limiting manner, of 2-methyl-5-aminophenol; 5-N-(β-hydroxyethyl)amino-2-methylphenol; 6-chloro-2-methyl-5-aminophenol, 3-aminophenol; 1,3-dihydroxybenzene; 1,3-dihydroxy-2-methylbenzene; 4-chloro-1,3-dihydroxybenzene; 2,4-diamino-1-(β-hydroxyethyloxy) benzene; 2-amino-4-(β-hydroxyethylamino)-1-methoxybenzene; 1,3-diaminobenzene; 1,3-bis(2,4-diaminophenoxy)propane; 3-ureidoaniline; 3-ureido-1-dimethylaminobenzene; sesamol; 1-β-hydroxyethylamino-3,4-methylenedioxybenzene; α-naphthol; 2-methyl-1-naphthol; 6-hydroxyindole; 4-hydroxyindole; 4-hydroxy-N-methylindole; 2-amino-3-hydroxypyridine; 6-hydroxybenzomorpholine 3,5-diamino-2,6-dimethoxypyridine; 1-N-(β-hydroxyethyl)amino-3,4-methylene dioxybenzene; 2,6-bis-(β-hydroxyethylamino)toluene, and the acid addition salts thereof.

The at least one oxidation coupler (C) can be present in an amount ranging from 0.001% to 20% by weight, for example from 0.005% to 10% by weight, and further for example from 0.01% to 5% by weight, relative to the total weight of the composition.

The compositions of the disclosure may also comprise at least one additional oxidation base.

According to the present disclosure, the term "additional oxidation base" is intended to mean at least one oxidation base different from the at least one oxidation base of diaminodiazacyclopentene type (B) mentioned above.

Non-limiting examples of these additional oxidation bases that can be used include para-phenylenediamines, bisphenylalkylenediamines, para-aminophenols, bis-para-aminophenols, ortho-aminophenols, heterocyclic bases other than the diaminodiazacyclopentene oxidation bases, and addition salts thereof.

Among the para-phenylenediamines, non-limiting mention may be made, for example, of para-phenylenediamine; para-toluoylenediamine; 2-chloro-para-phenylenediamine; 2,3-dimethyl-para-phenylenediamine; 2,6-dimethyl-para-phenylenediamine; 2,6-diethyl-para-phenylenediamine; 2,5-dimethyl-para-phenylenediamine; N,N-dimethyl-para-phenylenediamine; N,N-diethyl-para-phenylenediamine; N,N-dipropyl-para-phenylenediamine; 4-amino-N,N-diethyl-3-methylaniline; N,N-bis(β-hydroxyethyl)-para-phenylenediamine; 4-N,N-bis(β-hydroxyethyl)amino-2-methylaniline; 4-N,N-bis(β-hydroxyethyl)amino-2-chloroaniline; 2-β-hydroxyethyl-para-phenylenediamine; 2-fluoro-para-phenylenediamine; 2-isopropyl-para-phenylenediamine; N-(β-hydroxypropyl)-para-phenylenediamine; 2-hydroxymethyl-para-phenylenediamine; N,N-dimethyl-3-methyl-para-phenylenediamine; N,N-(ethyl-β-hydroxyethyl)-para-phenylenediamine; N-(β,γ-dihydroxypropyl)-para-phenylenediamine; N-(4'-aminophenyl)-para-phenylenediamine; N-phenyl-para-phenylenediamine; 2-β-hydroxyethyloxy-para-phenylenediamine; 2-β-acetylaminoethyloxy-para-phenylenediamine; N-(β-methoxyethyl)-para-phenylenediamine; 4-aminophenylpyrrolidine; 2-thienyl-para-phenylenediamine; 2-βhydroxyethylamino-5-aminotoluene; 3-hydroxy-1-(4'-aminophenyl)pyrrolidine, and the acid addition salts thereof.

Among the para-phenylenediamines mentioned above, further non-limiting mention may be made, for example, of para-phenylenediamine; para-toluylenediamine; 2-isopropyl-para-phenylenediamine; 2-β-hydroxyethyl-para-phenylenediamine; 2-β-hydroxyethyloxy-para-phenylenediamine; 2,6-dimethyl-para-phenylenediamine; 2,6-diethyl-para-phenylenediamine; 2,3-dimethyl-para-phenylenediamine; N,N-bis(β-hydroxyethyl)-para-phenylenediamine; 2-chloro-para-phenylenediamine; 2-β-acetylaminoethyloxy-para-phenylenediamine, and the acid addition salts thereof.

Among the bisphenylalkylenediamines, non-limiting mention may be made, for example, of N,N'-bis(β-hydroxyethyl)-N,N'-bis(4'-aminophenyl)-1,3-diaminopropanol; N,N'-bis(β-hydroxyethyl)-N,N'-bis(4'-aminophenyl) ethylenediamine; N,N'-bis(4-aminophenyl) tetramethylenediamine; N,N'-bis(β-hydroxyethyl)-N,N'-bis(4-aminophenyl)tetramethylenediamine; N,N'-bis-(4-methylaminophenyl)tetramethylenediamine; N,N'-bis(ethyl)-N,N'-bis(4'-amino-3'-methylphenyl) ethylenediamine; 1,8-bis(2,5-diaminophenoxy)-3,6-dioxaoctane; and the acid addition salts thereof.

Among the para-aminophenols, non-limiting mention may be made, for example, of para-aminophenol; 4-amino-3-methylphenol; 4-amino-3-fluorophenol; 4-amino-3-hydroxymethylphenol; 4-amino-2-methylphenol; 4-amino-2-hydroxymethylphenol; 4-amino-2-methoxymethylphenol; 4-amino-2-aminomethyl phenol; 4-amino-2-(β-hydroxyethylaminomethyl)phenol; 4-amino-2-fluorophenol; and the acid addition salts thereof.

Among the ortho-aminophenols, non-limiting mention may be made, for example, of 2-aminophenol; 2-amino-5-methyl phenol; 2-amino-6-methylphenol; 5-acetamido-2-aminophenol, and the acid addition salts thereof.

Among the heterocyclic bases non-limiting mention may be made, for example, of pyridine derivatives, pyrimidine derivatives, and addition salts thereof. Among the pyridine derivatives, non-limiting mention may be made, for example, of 2,5-diaminopyridine; 2-(4-methoxyphenyl)amino-3-aminopyridine; 2,3-diamino-6-methoxypyridine; 2-(β-methoxyethyl)amino-3-amino-6-methoxypyridine; 3,4-diaminopyridine; and the acid addition salts thereof. Such pyridine derivatives are described, for example, in United Kingdom Patent Nos. GB 1,026,978 and GB 1,153,196.

Other non-limiting examples of pyridine oxidation bases that can be used in the present disclosure are the 3-aminopyrazolo[1,5-a]pyridine oxidation bases and addition salts thereof described, for example, in French Patent Application No. FR 2801308. By way of non-limiting example, mention may be made of pyrazolo[1,5-a]pyridin-3-ylamine; 2-acetylaminopyrazolo-[1,5-a]pyridin-3-ylamine; 2-morpholin-4-ylpyrazolo[1,5-a]pyridin-3-ylamine; 3-aminopyrazolo[1,5-a]pyridine-2-carboxylic acid; 2-methoxypyrazolo[1,5-a]pyridin-3-ylamino; (3-aminopyrazolo[1,5-a]pyridin-7-yl) methanol; 2-(3-aminopyrazolo[1,5-a]pyridin-5-yl)ethanol; 2-(3-aminopyrazolo[1,5-a]pyridin-7-yl)ethanol; (3-aminopyrazolo-[1,5-a]pyridin-2-yl)methanol; 3,6-diaminopyrazolo[1,5-a]pyridine; 3,4-diaminopyrazolo[1,5-a]pyridine; pyrazolo[1,5-a]pyridine-3,7-diamine; 7-morpholin-4-ylpyrazolo[1,5-a]pyridin-3-ylamine; pyrazolo[1,5-a]pyridine-3,5-diamine; 5-morpholin-4-ylpyrazolo[1,5-a]pyridin-3-ylamine; 2-[(3-aminopyrazolo[1,5-a]pyridin-5-yl)(2-hydroxyethyl)amino]ethanol; 2-[(3-aminopyrazolo[1,5-a]pyridin-7-yl)(2-hydroxyethyl)amino]ethanol; 3-aminopyrazolo[1,5-a]pyridin-5-ol; 3-aminopyrazolo[1,5- a]pyridin-4-ol; 3-aminopyrazolo[1,5-a]pyridin-6-ol; 3-aminopyrazolo[1,5-a]pyridin-7-ol; and also addition salts thereof with an acid or with a base.

Non-limiting mention may be made among the pyrimidine derivatives of the compounds described, for example, in German Patent No. DE 2359399; Japanese Patent Nos. 88-169571 and JP 05-63124; European Patent No. 0 770 375 and International Patent Application No. WO 96/15765, such as 2,4,5,6-tetraminopyrimidine; 4-hydroxy-2,5,6-triaminopyrimidine; 2-hydroxy-4,5,6-triaminopyrimidine; 2,4-dihydroxy-5,6-diaminopyrimidine; 2,5,6-triaminopyrimidine; and pyrazolopyrimidine derivatives such as those mentioned in French Patent Application No. FR-A-2 750 048, and among which non-limiting mention may be made of pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol; 2-(7-aminopyrazolo[1,5-a]pyrimidin-3-ylamino)ethanol; 2-[(3-aminopyrazolo[1,5-a]pyrimidin-7-yl)(2-hydroxyethyl)amino]ethanol; 2-[(7-aminopyrazolo[1,5-a]pyrimidin-3-yl)(2-hydroxyethyl)amino]ethanol; 5,6-dimethylpyrazolo[1,5-a]pyrimidine-3,7-diamine; 2,6-dimethylpyrazolo[1,5-a]pyrimidine-3,7-diamine; 2,5,N7,N7-tetramethylpyrazolo-[1,5-a]pyrimidine-3,7-diamine; 3-amino-5-methyl-7-imidazolylpropylaminopyrazolo[1,5-a]pyrimidine; and addition salts thereof with an acid and tautomeric forms thereof when a tautomeric equilibrium exists.

The at least one additional oxidation base can be present in a total amount ranging from 0.001% to 10% by weight, for example from 0.005% to 6% by weight, relative to the total weight of the dye composition.

According to the present disclosure, the addition salts of the oxidation bases and of the couplers that can be used in the context of the present disclosure can be, by way of non-limiting example, chosen from acid addition salts, such as hydrochlorides, hydrobromides, sulfates, citrates, succinates, tartrates, lactates, tosylates, benzenesulfonates, phosphates, and acetates; and the addition salts with a base, such as sodium hydroxide, potassium hydroxide, aqueous ammonia, amines, or alkanolamines.

In at least one embodiment of the present disclosure, the additional oxidation bases used in the compositions according to the present disclosure are chosen from para-phenylenediamines and para-aminophenols, and addition salts thereof.

The dye composition in accordance with the present disclosure may also further comprise at least one direct dye that may, for example, be chosen from nitrobenzene dyes, azo direct dyes, methine direct dyes, anthraquinone dyes, xanthene dyes, triarylmethane dyes, and addition salts thereof. These direct dyes may be nonionic, anionic, or cationic in nature.

The medium used in the compositions according to the present disclosure can be chosen from an aqueous medium or a medium comprising water and at least one organic solvent.

The at least one organic solvent used in the compositions according to the present disclosure may be chosen from monohydroxylated alcohols and polyols.

By way of non-limiting example, the monohydroxylated alcohols that can be used in the compositions of the present disclosure can be chosen from $C_1$-$C_4$ lower alcohols, such as ethanol, isopropanol, tert-butanol, or n-butanol, and mixtures thereof. In at least one embodiment, the at least one organic solvent is ethanol.

By way of non-limiting example of polyols that can be used according to the present disclosure, mention may be made of propylene glycol, polyethylene glycols, and glycerol. By way of non-limiting example of organic solvents, mention may also be made of polyol ethers such as 2-butoxyethanol, propylene glycol monomethyl ether, diethylene glycol monoethyl ether, and diethylene glycol monomethyl ether; and also aromatic alcohols such as benzyl alcohol or phenoxyethanol, and mixtures thereof.

The at least one organic solvent in the compositions according to the present disclosure can be present, in a total amount, ranging form 0% to 30% by weight, for example from 0% to 20% by weight, relative to the total weight of the composition.

The compositions according to the present disclosure may further comprise at least one thickener, also referred to as a "rheology-adjusting agent," wherein the thickener is different from the at least one nonionic derivative of cellulose with at least one hydrophobic substituent according to the present disclosure.

The at least one rheology-adjusting agent, according to the present disclosure, may be chosen from mineral and organic thickeners, such as polymeric associative thickeners; fatty alcohols, such as oleyl alcohol; cellulosic derivatives other than the at least one nonionic derivative of cellulose with at least one hydrophobic substituent (A) according to the present disclosure, such as hydroxyethylcellulose, hydroxypropylcellulose, and carboxymethylcellulose; and gums of microbial origin, such as xanthan gum and scleroglucan gum.

According to one embodiment, the at least one rheology-adjusting agent is chosen from fatty alcohols, such as $C_{20}$-$C_{22}$ fatty alcohols, and cellulose derivatives, other than the at least one nonionic derivative of cellulose with at least one hydrophobic substituent (A) according to the present disclosure.

The at least one thickener can be present, in a total amount, ranging from 0.01% to 20% by weight, for example from 1% to 10% by weight, relative to the total weight of the composition.

The dye composition in accordance with the present disclosure may further comprise at least one adjuvant conventionally used in compositions for dyeing the hair.

As used herein, the term "adjuvant" is intended to mean at least one additive, different from the abovementioned compounds, such as anionic, cationic, nonionic, amphoteric, zwitterionic surfactants, or mixtures thereof; nonionic, amphoteric, zwitterionic, anionic, or cationic polymers, other than the at least one nonionic derivative of cellulose with at least one hydrophobic substituent (A) according to the present disclosure, or mixtures of said polymers; penetrating agents; sequestering agents; fragrances; buffers; dispersants; conditioning agents such as modified or unmodified, volatile or non-volatile silicones; film-forming agents; ceramides; preservatives; opacifiers; vitamins; amino acids; oligopeptides; peptides; modified or unmodified, hydrolysed or non-hydrolysed proteins; enzymes; branched or unbranched fatty acids and alcohols; animal, plant or mineral waxes; hydroxylated organic acids; UV screens; antioxidants and free-radical scavengers; antidandruff agents; seborrhoea-regulating agents; calmatives; mineral, plant or animal oils; polyisobutenes and poly($\alpha$-olefins); pigments; acids, bases, plasticizers, mineral fillers, pearlescent agents, flakes; antistatic agents; and reducing agents.

The at least one adjuvant as mentioned above may be present in an amount ranging from 0.01% to 40% by weight, for example from 0.1% to 25% by weight, relative to the weight of the composition.

Those skilled in the art will take care to select this (or these) possible additional compound(s) in such a way that the beneficial properties intrinsically associated with the oxidation dyeing composition in accordance with the present disclosure are not, or not substantially, impaired by the addition(s) envisaged.

The pH of the dye composition in accordance with the present disclosure, by way of non-limiting example, ranges from 3 to 12, such as from 5 to 11. The pH may be adjusted to the desired value via at least one acidifying agent or at least one basifying agent commonly used in the dyeing of keratin fibers or alternatively using at least one conventional buffer system.

Among the at least one acidifying agent, non-limiting mention may be made, by way of example, of mineral or organic acids such as hydrochloric acid, orthophosphoric acid, sulfuric acid, sulfonic acids, and carboxylic acids, for instance acetic acid, tartaric acid, citric acid, and lactic acid.

Among the at least one basifying agent, non-limiting mention may, by way of example, be made of aqueous ammonia; alkali metal carbonates; alkanolamines such as mono-, di-, and triethanolamines and derivatives thereof; sodium hydroxide or potassium hydroxide; and compounds of formula (III):

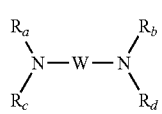

(III)

wherein:
W is a propylene residue optionally substituted with a hydroxyl group or a $C_1$-$C_4$ alkyl group;
$R_a$, $R_b$, $R_c$, and $R_d$, which may be identical or different, are independently chosen from hydrogen atoms, $C_1$-$C_4$ alkyl groups, and $C_1$-$C_4$ hydroxyalkyl groups.

The dye composition according to the present disclosure may be in various forms, such as in the form of creams or gels, or in any other form suitable for dyeing keratin fibers, such as human hair.

The process for dyeing keratin fibers, according to the present disclosure, is a process wherein the composition according to the present disclosure as defined above is applied to the fibers, and, in at least one embodiment, in the presence of at least one oxidizing agent for a period of time sufficient to develop the desired color. The color may be revealed at acidic, neutral, or alkaline pH and the at least one oxidizing agent may be added to the composition of the present disclosure just at the time of use, or it may be used starting from an oxidizing composition comprising the at least one oxidizing agent, applied simultaneously with or sequentially to the composition of the present disclosure.

According to at least one embodiment, the composition according to the present disclosure is a ready-to-use composition, wherein the dyeing composition is mixed, for example, at the time of use, with a composition comprising, in a medium suitable for dyeing, at least one oxidizing agent, the oxidizing agent being present in a sufficient amount to develop a coloration. The mixture obtained is subsequently applied to the keratin fibers. After a leave-on time ranging from 3 to 50 minutes, such as from 5 to 30 minutes, the keratin fibers are rinsed, washed with shampoo, rinsed again, and then dried.

The oxidizing agents conventionally used for the oxidation dyeing of keratin fibres are, for example, hydrogen peroxide; urea peroxide; alkali metal bromates; persalts such as perborates and persulfates; peracids; and oxidase enzymes, among which mention may be made of peroxidases, 2-electron oxidoreductases, such as uricases, and 4-electron oxygenases, such as laccases, these oxidoreductases being optionally combined with their customary cofactors, such as uric acid for uricases. In at least one embodiment of the present disclosure, the at least one oxidizing agent is hydrogen peroxide.

The oxidizing composition may further comprise at least one adjuvant conventionally used in compositions for dyeing the hair, as defined above.

The pH of the oxidizing composition comprising the at least one oxidizing agent, is such that, after mixing with the dye composition, the pH of the resulting composition applied to the keratin fibers may range from 3 to 12, for example from 5 to 10. The pH may be adjusted to the desired value via at least one acidifying agent or at least one basifying agent normally used in the dyeing of keratin fibers, as defined above.

The ready-to-use composition which may be applied to the keratin fibers may be in various forms, such as in the form of creams or gels, or in any other form suitable for dyeing keratin fibers, such as human keratin fibers, for example the hair.

Another aspect of the present disclosure is a multicompartment dyeing device or dyeing "kit", comprising at least one first compartment comprising at least one dye composition as defined in the foregoing disclosure and at least one second compartment comprising at least one oxidizing composition. This device may be equipped, by way of non-limiting example, with a mechanism for delivering the desired mixture to the hair, such as the devices described in French Patent Application No. FR-A-2 586 913.

As disclosed herein, the percentages stated are by weight.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements.

The examples that follow are intended to illustrate the present disclosure without, however, being limiting in nature.

EXAMPLES

Example 1

Dye Compositions According to the Present Disclosure

The following compositions 1 and 2 were prepared.

|  | Dye composition | |
|---|---|---|
|  | Composition 1 | Composition 2 |
| Cetyl hydroxyethylcellulose (POLYSURF ® 67 sold by the company Aqualon) | 0.4 g | — |
| Cetyl hydroxyethylcellulose (NATROSOL ® PLUS GRADE 330 CS sold by the company Aqualon) | — | 0.4 g |
| 2,3-Diamino-6,7-dihydro-1H,5H-pyrazolo[1,2-a]pyrazol-1-one, 2CH$_3$SO$_3$H | 1.9 g | — |
| 4,5-Diamino-1-(2-hydroxyethyl)-1H-pyrazole sulphate | — | 1.9 g |
| para-Aminophenol | 0.1 g | — |
| 4-Amino-2-hydroxytoluene | 0.2 g | 1.4 g |
| 5-Amino-6-chloro-ortho-cresol | 0.8 g | 0.2 g |
| para-Phenylenediamine | — | 0.3 g |
| Stearic acid monoethanolamide | 4.8 g | 4.8 g |
| Oleic acid | 3 g | 3 g |
| Aqueous solution comprising 20% by weight of NH$_3$ | 7 g | 2.1 g |
| TiO$_2$ | 0.3 g | 0.3 g |
| Monoethanolamine | 6.5 g | 6.3 g |
| Oleth-10 | 1.8 g | 1.8 g |
| Aqueous solution comprising 40% by weight of polyquaternium-6 (MERQUAT ® 100 sold by the company Ondeo) | 1.6 g | 1.6 g |
| Ethylenediaminetetraacetic acid (EDTA) | 0.2 g | 0.2 g |
| Aqueous solution comprising 60% by weight of hexadimethrine chloride (MEXOMERE ® PO sold by the company Chimex) | 1.2 g | 1.2 g |
| Hydroxypropylmethylcellulose | 0.2 g | 0.2 g |
| Oleth-30 | 1.5 g | 1.5 g |
| Steareth-2 | 5.5 g | 5.5 g |
| C$_{20}$-C$_{22}$ alcohols (NAFOL ® 2022 EN sold by the company Sasol) | 3 g | 3 g |
| Reducing agent | q.s. | q.s. |
| Demineralized water q.s | 100 g | 100 g |

Application Protocol

Each of Composition 1 and 2 was diluted, extemporaneously, with one and a half times its weight of an oxidizing composition having a pH in the region of 3 (aqueous hydrogen peroxide at 20 volumes) (6% by weight of H$_2$O$_2$). The mixture was easily prepared and had a good viscosity; it was easily applied to grey hair, comprising 90% white hairs, at a rate of 10 g per 1 g of hair, for 30 minutes. The hair was then rinsed, washed with a standard shampoo, and dried.

The hair coloration was evaluated visually. The results obtained on natural grey hair, comprising 90% white hairs, after treatment, were the following:

|  | Shade |
|---|---|
| Composition 1 | Strong coppery |
| Composition 2 | Strong coppery red |

These colorations had good properties in terms of selectivity, strength, stability, and fastness.

Example 2

Comparative Testing

Composition 3 according to the present disclosure and Comparative Composition 4 were prepared.

|  | Dye composition | |
|---|---|---|
|  | Composition 3 (inventive) | Composition 4 (comparative) |
| Oxyethylenated oleocetyl alcohol comprising 30 mol of ethylene oxide | 1.5 g | 1.5 g |
| 2,3-Diamino-6,7-dihydro-1H,5H-pyrazolo[1,2-a]pyrazol-1-one dimethanesulphonate | 1 g | 1 g |
| Stearamide monoethanolamine, monoethanolamine, stearic acid (96:2:2) | 5 g | 5 g |
| Polymer of methylenebis(4-cyclohexylisocyanate) (SMDI)/polyethylene glycol with a decyl ending, in an aqueous-glycolic solution at 35% by weight of active material (am) relative to the total weight of the solution | — | 0.45 g am |
| Sodium sulphite | 0.5 g | 0.5 g |
| Ethylenediaminetetraacetic acid (EDTA) | 0.2 g | 0.2 g |
| Pure monoethanolamine | 1.05 g | 1.05 g |
| 1-Methyl-2-hydroxy-4-aminobenzene | 0.36 g | 0.36 g |
| Erythorbic acid (or D-isoascorbic acid) | 0.5 g | 0.5 g |
| Hydroxyethylcellulose with a C$_{14}$/C$_{16}$ alkyl substituent | 0.45 g am | — |
| Aqueous ammonia (20% reference concentration of ammonia) | 10 g | 10 g |
| Oxyethylenated stearyl alcohol comprising 2 mol of ethylene oxide | 5.5 g | 5.5 g |
| Oleic acid | 3 g | 3 g |
| Deionized water | qs 100 g | qs 100 g |

Application Protocol

At the time of use, each of Compositions 3 and 4 was mixed with one and a half times its weight of an oxidizing composition (aqueous hydrogen peroxide at 20 volumes) (6% by weight of H$_2$O$_2$).

Each mixture was applied to natural (NW) and permanent-waved (PW) locks of hair comprising 90% white hairs, at a rate of 15 g of mixture per gram of locks of hair. After a leave-on time of 30 minutes at ambient temperature, the locks were rinsed, washed with a standard shampoo, rinsed again, and dried.

The colorimetric measurements were carried out using the Konica Minolta CM-2600d spectrocolorimeter in the CIE L*a*b* system. In the L* a* b* system, L* represents the strength of the coloring obtained; the lower the value of L*, the stronger the coloring obtained. The chromaticity is measured by the values a* and b*, a* indicating the value along the green/red color axis and b* indicating the value along the blue/yellow color axis.

For each composition, the selectivity of the coloring was evaluated. The selectivity of the coloring is the variation in the color between natural hair and permanent-waved hair. The natural hair is representative of the nature of the hair at the root, whereas the permanent-waved hair is representative of the nature of the hair at the tip.

The selectivity is measured by ΔE, which is the variation in color between the natural hair and the permanent-waved hair, and is obtained from the formula:

$$\Delta E = \sqrt{(L^* - L_o^*)^2 + (a^* - a_o^*)^2 + (b^* - b_o^*)^2}$$

wherein:

L*, a*, and b* represent the parameters of the dyed permanent-waved hair, and $L_0^*$, $a_0^*$, and $b_0^*$ represent the parameters of the dyed natural hair.

The lower the value of ΔE, the lower the selectivity and therefore the more uniform the coloring along the hair.

Results

|  | Hair type | L* | a* | b* | ΔE |
|---|---|---|---|---|---|
| Composition 3 (inventive) | NW dyed | 43.68 | 21.04 | 31.14 | 13.19 |
|  | PW dyed | 39.04 | 31.56 | 37.61 |  |
| Composition 4 (comparative) | NW dyed | 48.28 | 21.78 | 34.65 | 16.15 |
|  | BP dyed | 33.78 | 24.16 | 27.96 |  |

Composition 3, according to the present disclosure, resulted in stronger coloring on natural hair and also in lower selectivity.

What is claimed is:

1. A dye composition for keratin fibers, comprising, in a medium suitable for dyeing:
   (A) at least one nonionic derivative of cellulose comprising at least one hydrophobic substituent containing from 8 to 30 carbon atoms;
   (B) at least one oxidation base chosen from diaminodiazacyclopentene derivatives, and addition salts thereof; and
   (C) at least one oxidation coupler.

2. The dye composition according to claim 1, wherein the at least one nonionic derivative of cellulose is chosen from hydroxyethylcelluloses substituted with at least one hydrophobic substituent containing from 8 to 30 carbon atoms.

3. The dye composition according to claim 1, wherein the at least one hydrophobic substituent is chosen from $C_{10}$-$C_{22}$ alkyl groups.

4. The dye composition according to claim 1, wherein the at least one hydrophobic substituent is chosen from cetyl groups.

5. The dye composition according to claim 1, wherein the degree of hydrophobic substitution ranges from 0.1% to 10% by weight, relative to the total weight of the polymer.

6. The dye composition according to claim 1, wherein the concentration of the at least one nonionic derivative of cellulose ranges from 0.01% to 10% by weight, relative to the total weight of the composition.

7. The dye composition according to claim 1, wherein the at least one diaminodiazacyclopentene derivative is chosen from diaminopyrazolone derivatives.

8. The dye composition according to claim 7, wherein the at least one diaminopyrazolone derivative is chosen from compounds of formula (I):

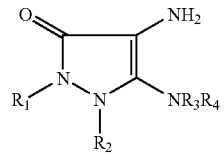

(I)

wherein:

$R_1$, $R_2$, $R_3$, and $R_4$, which may be identical or different, are each independently chosen from:

hydrogen atoms;

linear and branched $C_1$-$C_{10}$ alkyl groups, optionally substituted with at least one group chosen from $OR_5$, $NR_6R_7$, carboxyl, sulfonic, carboxamido $CONR_6R_7$, sulfonamido $SO_2NR_6R_7$, aliphatic heterocycles, and aryls optionally substituted with at least one group chosen from $C_1$-$C_4$ alkyl, hydroxyl, $C_1$-$C_2$ alkoxy, amino, and (di)($C_1$-$C_2$)alkylamino groups;

aryl groups optionally substituted with at least one group chosen from $C_1$-$C_4$ alkyl, hydroxyl, $C_1$-$C_2$ alkoxy, amino, and (di)($C_1$-$C_2$)alkylamino groups; and heteroaryl groups comprising 5 or 6 ring members, optionally substituted with at least one group chosen from $C_1$-$C_4$ alkyl and $C_1$-$C_2$ alkoxy groups;

a $R_5$, $R_6$, and $R_7$, which may be identical or different, are each independently chosen from:

hydrogen atoms;

linear and branched $C_1$-$C_4$ alkyl groups optionally substituted with at least one group chosen from hydroxyl, $C_1$-$C_2$ alkoxy, carboxamido $CONR_8R_9$, sulfonyl $SO_2R_8$ groups, and aryl groups optionally substituted with a group chosen from $C_1$-$C_4$ alkyl, hydroxyl, $C_1$-$C_2$ alkoxy, amino, and (di)($C_1$-$C_2$)alkylamino groups;

aryl groups optionally substituted with at least one group chosen from $C_1$-$C_4$ alkyl, hydroxyl, $C_1$-$C_2$ alkoxy, amino, and (di)($C_1$-$C_2$)alkylamino groups;

carboxamido groups $CONR_8R_9$; and sulfonyl groups $SO_2R_8$;

$R_8$ and $R_9$, which may be identical or different, are each independently chosen from hydrogen atoms; and linear and branched $C_1$-$C_4$ alkyl groups optionally substituted with at least one group chosen from hydroxyl and $C_1$-$C_2$ alkoxy groups;

$R_1$ and $R_2$ on the one hand, and $R_3$ and $R_4$, on the other hand, may also form, together with the nitrogen atom(s) to which they are attached, a saturated or unsaturated heterocycle comprising from 5 to 7 ring members, optionally substituted or N-substituted with at least one group chosen from halogen atoms, amino, (di)($C_1$-$C_4$) alkylamino, (di)hydroxy($C_1$-$C_2$)alkylamino, hydroxyl, carboxyl, carboxamido, (di)($C_1$-$C_2$)alkylcarboxamido and $C_1$-$C_2$ alkoxy groups, and $C_1$-$C_4$ alkyl groups optionally substituted with at least one group chosen from hydroxyl, amino, (di)alkylamino, alkoxy, carboxyl, and sulfonyl groups; it being possible for said heterocycles formed by $R_1$ and $R_2$, on the one hand, and $R_3$ and $R_4$, on the other hand, with the nitrogen atom(s) to which they are attached, to be identical or different, and it being possible for the ring members forming said heterocycles to be chosen from carbon, nitrogen, and oxygen atoms.

9. The dye composition according to claim 8, wherein the diaminopyrazolone derivative of formula (I) is 2,3-diamino-6,7-dihydro-1H,5H-pyrazolo[1,2-a]pyrazol-1-one or an addition salt thereof.

10. The dye composition according to claim 1, wherein the at least one diaminodiazacyclopentene derivative is chosen from diaminopyrazole derivatives.

11. The dye composition according to claim 10, wherein the at least one diaminopyrazole derivative is chosen from compounds of formula (II):

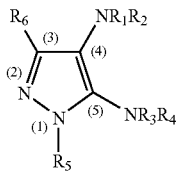

(II)

wherein:

$R_1$, $R_2$, $R_3$, $R_4$, and $R_5$, which may be identical or different, are each independently chosen from hydrogen atoms; $C_1$-$C_6$ alkyl radicals optionally substituted with at least one substituent chosen from OR, NHR, NRR', SR, SOR, $SO_2R$, COR, COOH, $CONH_2$, CONHR, CONRR', $PO(OH)_2$, SH, $SO_3X$, a noncationic heterocycle, Cl, Br, and I;

X is chosen from a hydrogen atom, Na, K, and $NH_4$; and

R and R', which may be identical or different, are each independently chosen from $C_1$-$C_4$ alkyl and alkenyl groups; $C_2$-$C_4$ hydroxyalkyl radicals; $C_2$-$C_4$ aminoalkyl radicals; phenyl radicals optionally substituted with a group chosen from halogen atoms, $C_1$-$C_4$ alkyl, $C_1$-$C_4$ alkoxy, nitro, trifluoromethyl, amino, and $C_1$-$C_4$ alkylamino radicals; benzyl radicals optionally substituted with an entity chosen from halogen atoms, $C_1$-$C_4$ alkyl, $C_1$-$C_4$ alkoxy, methylenedioxy, and amino radicals; and the radicals:

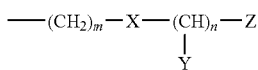

wherein m and n are integers, which may be identical or different, ranging from 0 and 3 inclusive; X is an oxygen atom or NH; Y is chosen from a hydrogen atom and $C_1$-$C_4$ alkyl radicals; Z is chosen from a methyl radical when n is equal to 0, or $C_1$-$C_4$ alkyl radicals, OR, and NR"R''' groups when n is greater than or equal to 1; R" and R''', which may be identical or different, are each independently chosen from a hydrogen atom and $C_1$-$C_4$ alkyl radicals; or $R_9$ forms, with the nitrogen atom of the $NR_7R_8$ group at position 5, a heterocycle comprising at least 4 ring members, $R_6$ is chosen from $C_1$-$C_6$ alkyl radicals; $C_1$-$C_4$ hydroxyalkyl radicals; $C_1$-$C_4$ aminoalkyl radicals; ($C_1$-$C_4$)alkylamino($C_1$-$C_4$)alkyl radicals; di($C_1$-$C_4$)alkylamino($C_1$-$C_4$)alkyl radicals; hydroxy($C_1$-$C_4$)alkylamino($C_1$-$C_4$)alkyl radicals; ($C_1$-$C_4$)alkoxymethyl radicals; phenyl radicals; phenyl radicals substituted with an entity chosen from halogen atoms, ($C_1$-$C_4$)alkyl, ($C_1$-$C_4$)alkoxy, nitro, trifluoromethyl, amino, and ($C_1$-$C_4$)alkylamino radicals; benzyl radicals; benzyl radicals substituted with a group chosen from halogen atoms, ($C_1$-$C_4$)alkyl, ($C_1$-$C_4$)alkoxy, nitro, trifluoromethyl, amino, and ($C_1$-$C_4$)alkylamino radicals; heterocycles chosen from thiophene, furan, and pyridine; and —$(CH_2)_p$—O—$(CH_2)_q$—OR" radicals, wherein p and q are integers, which may be identical or different, ranging from 1 and 3 inclusive, and R" is as defined above, it being understood that at least one of the radicals $R_1$, $R_2$, $R_3$, and $R_4$ is a hydrogen atom.

12. The dye composition according to claim 11, wherein the at least one diaminopyrazole derivative of formula (II) is 4,5-diamino-1-(2-hydroxyethyl)-1H-pyrazole or an addition salt thereof.

13. The dye composition according to claim 1, wherein the at least one oxidation base is present in an amount ranging from 0.001% to 20% by weight, relative to the total weight of the composition.

14. The dye composition according to claim 1, wherein the at least one oxidation coupler is chosen from benzene couplers, heterocyclic couplers, naphthalene couplers, and addition salts thereof.

15. The dye composition according to claim 14, wherein the at least one benzene coupler chosen from meta-aminophenols, meta-phenylenediamines, meta-diphenols, and addition salts thereof.

16. The dye composition according to claim 1, wherein the at least one oxidation coupler is present in an amount ranging from 0.005% to 15% by weight, relative to the total weight of the composition.

17. The dye composition according to claim 1, further comprising at least one additional oxidation base, other than the at least one diaminodiazacyclopentene derivative, chosen from benzene oxidation bases and heterocyclic bases.

18. The dye composition according to claim 17, wherein the at least one additional oxidation base is a benzene oxidation base chosen from ortho- and para-phenylenediamines, bisphenylalkylenediamines, para-aminophenols, bis-para-aminophenols, ortho-aminophenols, and addition salts thereof.

19. The dye composition according to claim 1, further comprising at least one direct dye chosen from nitrobenzene dyes, azo direct dyes, methine direct dyes, anthraquinone dyes, xanthene dyes, triarylmethane dyes, and addition salts thereof.

20. The dye composition according to claim 1, further comprising at least one oxidizing agent.

21. A process for the oxidation dyeing of keratin fibers, comprising applying to the fibers, in the presence of at least one oxidizing agent for a period of time sufficient to develop the desired color, a dye composition, comprising, in a medium suitable for dyeing:
(A) at least one nonionic derivative of cellulose containing at least one hydrophobic substituent comprising from 8 to 30 carbon atoms;
(B) at least one oxidation base chosen from diaminodiazacyclopentene derivatives, and addition salts thereof; and
(C) at least one oxidation coupler.

22. A multi-compartment device, comprising, at least one first compartment containing at least one dye composition comprising, in a medium suitable for dyeing:
(A) at least one nonionic derivative of cellulose comprising at least one hydrophobic substituent containing from 8 to 30 carbon atoms;
(B) at least one oxidation base chosen from diaminodiazacyclopentene derivatives, and addition salts thereof; and
(C) at least one oxidation coupler;
and at least one second compartment containing at least one oxidizing agent.

* * * * *